United States Patent [19]
Vo

[11] Patent Number: 5,171,306
[45] Date of Patent: Dec. 15, 1992

[54] EYEDROP DELIVERY SYSTEM

[76] Inventor: Van T. Vo, 34 Bridge St., Lexington, Mass. 02173

[21] Appl. No.: 668,881

[22] Filed: Mar. 13, 1991

[51] Int. Cl.$^5$ ............................................. A61M 35/00
[52] U.S. Cl. ................................... 604/295; 604/298; 604/300
[58] Field of Search ............... 604/289, 296, 294, 295, 604/296, 297, 298, 300, 27, 28, 30-34, 131-134, 140, 141, 146, 147, 151, 152, 153, 154, 245-250

[56] References Cited

U.S. PATENT DOCUMENTS

| | | | |
|---|---|---|---|
| 4,697,785 | 10/1987 | Tuseth | 604/34 |
| 4,798,599 | 1/1989 | Thomas | 604/297 |
| 4,908,024 | 3/1990 | Py | 604/300 |
| 4,935,005 | 6/1990 | Haines | 604/30 |

FOREIGN PATENT DOCUMENTS

| | | | |
|---|---|---|---|
| 0147527 | 7/1985 | European Pat. Off. | 604/295 |
| 3441081 | 5/1986 | Fed. Rep. of Germany | 604/132 |

OTHER PUBLICATIONS

Dolman, Claes H, et al., "Mobil Infusion Pumps for Continuous Delivery of Fluid and Therapeutic Agents to the Eye", Annals of Opth., Feb. 1971, pp. 126-128.

Primary Examiner—David Isabella
Assistant Examiner—K. Reichle
Attorney, Agent, or Firm—Pandiscio & Pandiscio

[57] ABSTRACT

An eyedrop delivery system for administering eyedrops to at least one eye of a user, wherein the system comprises a fluid reservoir for holding a supply of eyedrop fluid, a tube for conducting eyedrop fluid from the fluid reservoir to at least one eye of the user, the tube comprising at least one distal end portion terminating adjacent the at least one eye of the user, fluid driving apparatus for continuously urging eyedrop fluid from the fluid reservoir through the tube toward the at least one distal end portion of the tube, and fluid control apparatus for successively (1) permitting eyedrop fluid to flow freely through the tube so that the eyedrop fluid can begin to exit the at least one distal end portion of the tube, (2) interfering with the flow of eyedrop fluid through the tube so as to prohibit any further eyedrop fluid from exiting the at least one distal end portion of the tube, and so as to cause the eyedrop fluid leaving the at least one distal end portion of the tube to exit the at least one distal end portion of the tube as a discrete eyedrop, and (3) withdrawing the fluid remaining in the tube away from the at least one distal end portion of the tube so that the distal-most portion of the fluid is disposed within, and is substantially engulfed by, the tube, whereby the distal-most portion of the fluid can create a super-saturated vapor condition at that point in the tube.

20 Claims, 8 Drawing Sheets

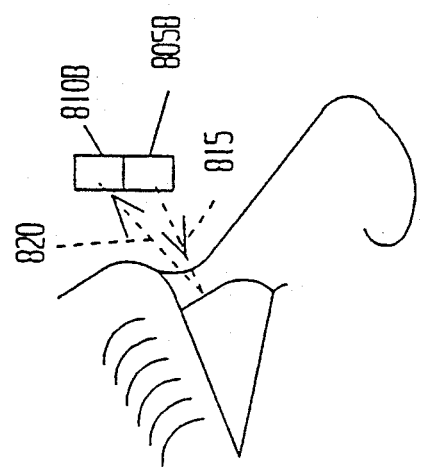
FIG. 6C
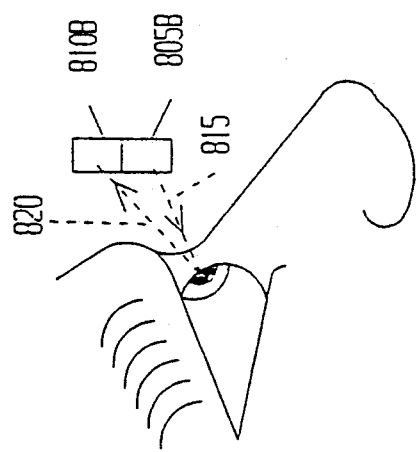
FIG. 6B
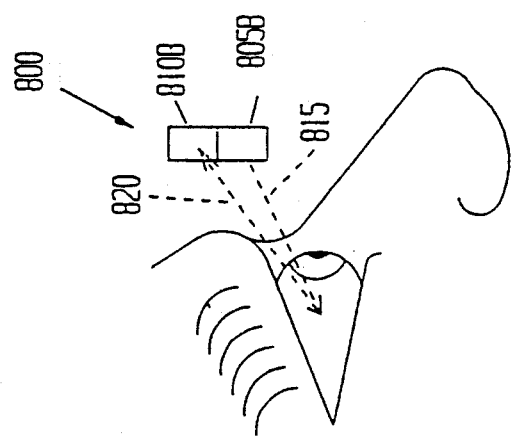
FIG. 6A
FIG. 6

EYEDROP DELIVERY SYSTEM

FIELD OF THE INVENTION

The present invention relates to medical devices in general, and more particularly to eyedrop delivery systems for administering eyedrops to the eyes.

BACKGROUND OF THE INVENTION

Many eye diseases such as glaucoma and dry eye are topically treated with eyedrop solutions. The frequency and duration of eyedrop therapy is dependent on the type of disease being treated and the individual patient's specific needs. For example, some diseases require continuous eyedrop application for the life of the patient, whereas others require frequent eyedrop application for relatively short periods of time. Such topical treatment of an eye disease is only effective if the eyedrops are properly administered to the eyes at the frequency and for the duration required by a particular patient and disease.

Since it can be inconvenient to manually apply eyedrop solutions with the necessary frequency and duration, and since some patients exhibit a reluctance or disregard for the consistent application of such medications, a number of eyedrop delivery systems have been developed which automatically apply the necessary medication to the eyes without patient intervention. Presently, there are four basic types of eyedrop delivery systems which have been developed. Such systems include insert devices, externally worn devices, semi-implants and full implants. Unfortunately, however, each of the present systems has proven unsatisfactory for proper and effective administration of eyedrop therapy.

Insertable systems generally consist of impregnating a contact lens-like matrix with medication and then placing the drug-impregnated contact lens-like matrix on the surface of the eye. The medication is then distributed over the eye by the blinking motion of the eyelid. This insert technique initially requires the presence of some natural tears (or an artificial moistener) for insertion of the device, as well as subsequent continuous voluntary blinking to distribute the medication. This method has also been known to cause discomfort and can be costly. Moreover, the insert technique cannot be utilized when a relatively large volume of fluid is required for proper treatment.

Externally worn devices generally comprise a system whereby fluid is transported from a fluid reservoir to the eyes via tubing which is mounted on some type of support structure, e.g. eyeglass frames, which is worn by the patient. Several different arrangements of externally worn devices have been proposed.

One arrangement features a fluid reservoir mounted directly on the support structure. Fluid flow to the eyes is activated by precise positioning and nodding of the head. With this system, fluid flow to the eyes is relatively unmanageable and unreliable.

Another arrangement has one end of the tubing positioned on the lower eyelid, or in the cul-de-sac of the conjunctivia, and the other end of the tubing connected to the fluid reservoir which is contained within a syringe whose plunger is activated by compressed gas generated by an electrolytic process. This arrangement can irritate and even injure the eye. Another disadvantage of this device is the toxicity of the electrolyte which is used to generate the gas which activates the plunger. Both the toxic electrolyte and the fluid reservoir are contained in the same syringe, thereby creating a risk of contamination of the fluid supply. This system also requires tedious maintenance which cannot be performed by the average patient.

A further arrangement of externally worn devices features a contact lens-like device adapted to be connected to the end of the tubing. Blinking motion of the eyelid compresses the contact lens/tube assembly to distribute solution over the surface of the eye. Such devices are uncomfortable to wear, require continuous voluntary blinking and are susceptible to contamination.

The semi-implant device is similar to a number of the foregoing in the sense that tubing is used to transport fluid from a reservoir to the eyes; however, part of the tubing is surgically implanted under the skin around the eyes and the tip of the tubing is surgically secured in the conjunctival area. This technique eliminates the need for eyeglasses or other support structure adjacent the eyes, but exposes the patient to the risks associated with surgical intervention.

The full implant device consists of implanting the whole system (i.e., pump, reservoir, and tubing) under the skin. This technique also exposes the patient to the risks associated with surgical intervention.

OBJECTS OF THE INVENTION

The principal object of the present invention is to provide a new and improved eyedrop delivery system for administering eyedrops to the eyes which overcomes the aforementioned disadvantages associated with prior art systems.

Another object of the present invention is to provide a new and improved eyedrop delivery system which is portable.

An additional object of the present invention is to provide a new and improved eyedrop delivery system which is simple to use and maintain.

Still another object of the present invention is to provide a new and improved eyedrop delivery system which is comfortable to wear.

Yet another object of the present invention is to provide a new and improved eyedrop delivery system which will automatically distribute eyedrops to the eyes at a programmable rate.

And still another object of the present invention is to provide a new and improved eyedrop delivery system which will distribute eyedrops to the eyes on demand.

A further object of the present invention is to provide a new and improved eyedrop delivery system which can control the velocity, volume and frequency of the eyedrop deployment.

Yet another object of the present invention is to provide a new and improved eyedrop delivery system which can detect eye and eyelid position and coordinate eyedrop delivery with the same so that the system will only deliver eyedrops when the eyes are open and in proper position.

Another object of the present invention is to provide a new and improved eyedrop delivery system which is non-clogging.

A further object of the present invention is to provide a new and improved eyedrop delivery system which is inexpensive.

And still another object of the present invention is to provide a new and improved eyedrop delivery system which is able to deliver eyedrops to both eyes simultaneously.

SUMMARY OF THE INVENTION

These and other objects of the present invention are addressed by a new and improved eyedrop delivery system for administering eyedrops to the eyes which comprises a fluid reservoir for holding a supply of the eyedrop fluid, tubing means for conducting the fluid from the fluid reservoir to at least one eye of the user, the tubing means comprising at least one distal end portion terminating adjacent the at least one eye of the user, and fluid control means for selectively (1) driving the fluid from the fluid reservoir through the tubing means so that discrete eyedrops exit the at least one distal end portion of the tubing means and are administered to the at least one eye of the user, and (2) withdrawing the fluid remaining in the tubing means away from the at least one distal end portion of the tubing means so that the distal-most portion of the fluid is disposed within, and is substantially engulfed by, the tubing means, whereby the distal-most portion of the fluid may create a super-saturated vapor condition at that point in the tubing means.

In the preferred embodiment of the invention, the tubing means comprises a resilient hollow tube, and the fluid control means comprises driving means for continuously driving fluid from the fluid reservoir towards the at least one eye of the user through the tubing means, and rotating wiper means for selectively engaging the tube so as to press against it and close it off at the point of engagement. More particularly, the rotating wiper means are adapted to selectively engage the tube along a travelling point of engagement, wherein the point of engagement travels in a direction opposite to the flow of fluid through the tube, and wherein the point of engagement can be stopped and held in position when desired, whereby the rotating wiper means can successively (1) first permit fluid to flow through the tube uninterrupted so as to begin to exit the at least one distal end portion of the tubing means, (2) thereafter engage the tube at a first point of engagement so as to halt the flow of fluid through the tube and thereby cause the fluid leaving the at least one distal end portion of the tubing means to be in the form of an eyedrop, (3) next sweep along the tube along a travelling point of engagement so as to withdraw the fluid remaining in the tubing means away from the at least one distal end of the tubing means, and (4) thereafter halt in engagement with the tube at a rest position so as to halt all fluid movement in the tube until the next eyedrop is to be released, whereupon the foregoing process is repeated.

Preferably the system also comprises eye and eyelid detecting means for detecting the positions of the eyes and eyelids prior to eyedrop ejection and preventing eyedrop ejection when the eyes are in a disadvantageous position or the eyelids are closed.

BRIEF DESCRIPTION OF THE DRAWINGS

Still other objects and features of the present invention will be more fully disclosed or rendered obvious in the following detailed description of the invention, which is to be considered together with the accompanying drawings wherein:

FIGS. 6A-6C are schematic representations of the eye and eyelid detecting means, showing the eye and eyelid of a user in different positions;

DETAILED DESCRIPTION OF THE INVENTION

Figure 1:
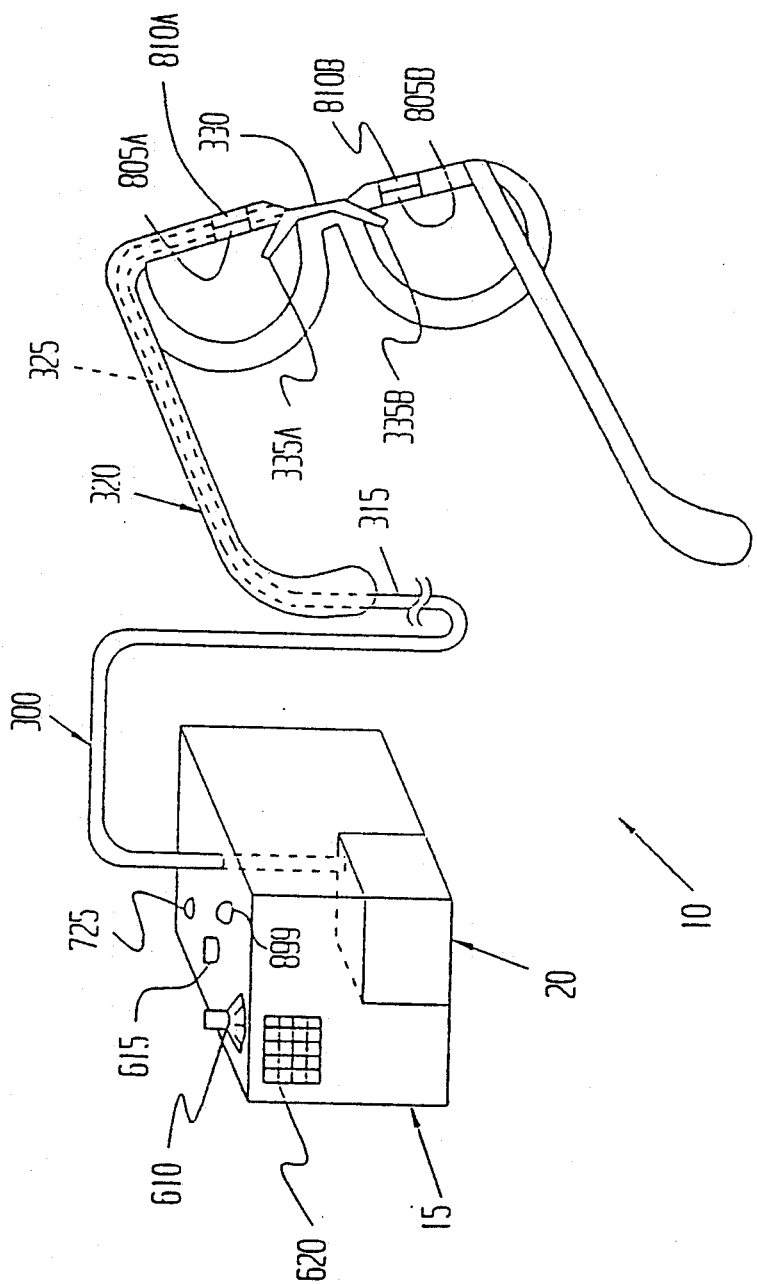
FIG. 1 is a perspective view of the preferred embodiment of the present invention.
Figure 2:
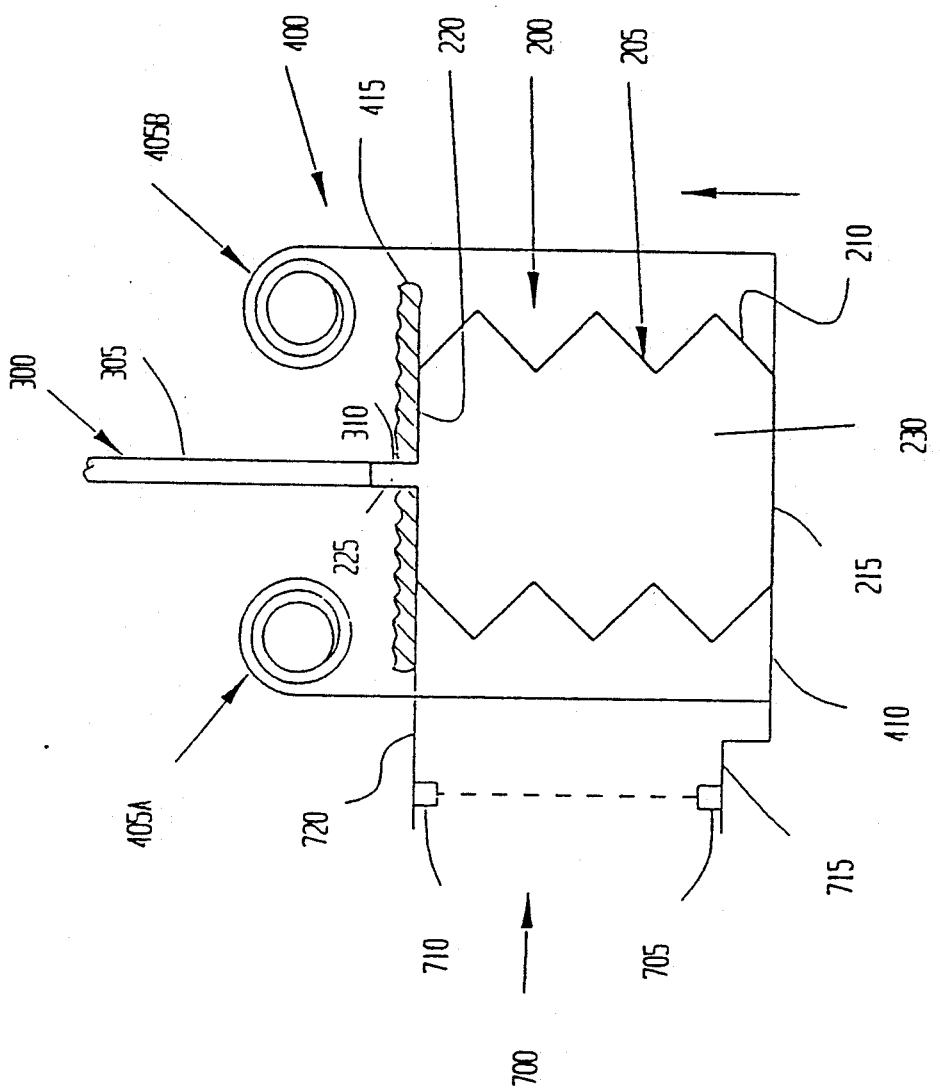
FIG. 2 is a side view of the fluid reservoir and fluid driving means.
Figure 3:
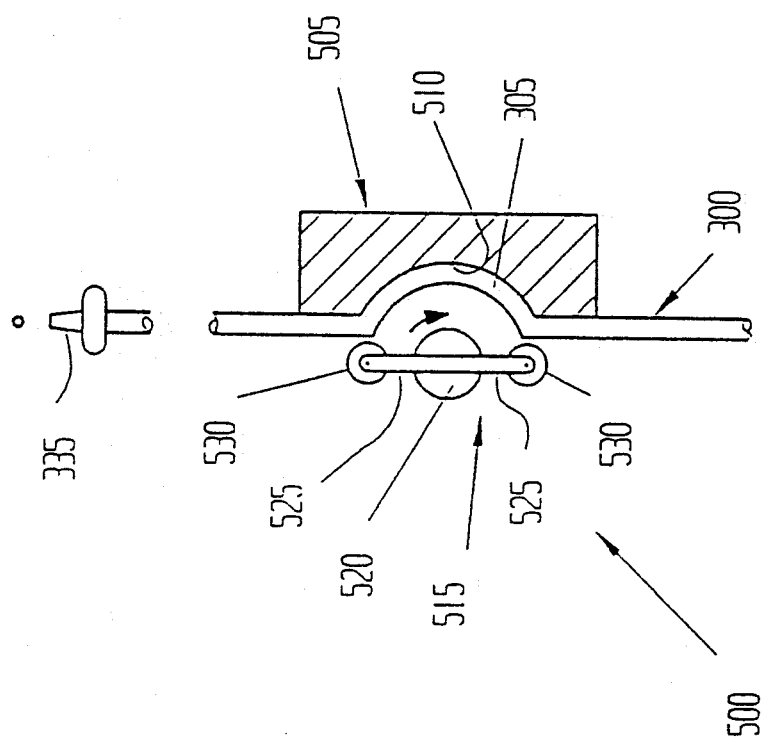
FIG. 3 is a side view of the rotating wiper means.

Looking first at FIGS. 1-3, there is shown an eyedrop delivery system 10 which comprises the preferred embodiment of the present invention. Eyedrop delivery system 10 generally comprises a case 15 (FIG. 1) for housing selected elements of the system, a fluid reservoir 200 (FIG. 2) for holding a supply of the eyedrop fluid which is to be administered to the eyes, tubing means 300 (FIGS. 1, 2 and 3) for conducting the fluid from the fluid reservoir 200 to the eyes, fluid driving means 400 (FIG. 2) for continuously driving the fluid from fluid reservoir 200 toward the eyes, and rotating wiper means 500 (FIG. 3) for generating discrete eyedrops out of the fluid flowing in tubing means 300 so that discrete eyedrops exit the tubing means and are administered to the eyes, and for controlling the location of the distal-most portion of the fluid in tubing means 300 between eyedrop ejections, as will hereinafter be discussed in further detail. Preferably fluid reservoir 200 and fluid driving means 400 are contained in a single cartridge unit 20 (FIG. 1) which may be quickly and easily attached and detached from housing 15 and the remainder of system 10, whereby fluid reservoir 200 may be easily replaced or refilled with eyedrop fluid.

Looking next at FIG. 2, fluid reservoir 200 comprises a bellows-type container 205 having compressible side walls 210, a movable floor or base 215, an immovable top or roof 220 and an outflow opening or port 225. Reservoir 200 is adapted to hold a supply of eyedrop fluid in its interior space 230, and its outflow opening 225 is connected to one end of a hollow tube 305 which forms part of tubing means 300. On account of this construction, it will be seen that the eyedrop fluid held in container 205 can flow out of container 205 and directly into tube 305.

Looking next at FIGS. 1-3, tubing means 300 comprises the aforementioned hollow tube 305. Tube 305 has a proximal end 310 (FIG. 2) which is connected to the outflow opening 225 of container 205, and a distal end 315 (FIG. 1) which is connected to a pair of eyeglasses 320. More specifically, the distal end 315 of tube 305 is connected to an interior passageway 325 which is formed in eyeglasses 320, wherein interior passageway 325 runs from tube 305 through the frame of eyeglasses 320 to a T-type connector 330 which is positioned on the bridge of eyeglasses 320. T-type connector 330 is in turn connected to a pair of nozzles 335A, 335B which are positioned on the eyeglasses so that when the eyeglasses are worn by a user, one nozzle will be presented to each eye. In this way fluid exiting container 205 through its outflow opening 225 will flow through hollow tube 305, along interior passageway 325, through T-type connector 330 and out nozzles 335A, 335B so that it enters the user's eyes. As will hereinafter be discussed in further detail, at least the portion of tube 305 residing adjacent rotating wiper means 500 is flexible. In the preferred embodiment of the invention, tubing 305 is preferably flexible along its entire length and is made of a suitable, vapor-impermeable material such as TEFLON (or some other form of tetrafluoroethylene) or polyethylene. Furthermore, in the preferred embodiment, nozzles 335A, 335B are made of a suitably soft, flexible, deformable material (e.g. SILASTIC or some other form of silicon rubber so that nozzles 335A, 335B can be manually adjusted to precisely direct the eyedrops exiting the nozzles directly into the eyes of each individual user. Inasmuch as nozzles 335A, 335B are intended to sit directly in front of, and in close proximity to, the eyes, it will be appreciated that the nozzles should be formed out of a material which is sufficiently soft and flexible so as to minimize the possibility of injury to the eyes in the case of accidents.

Fluid driving means 400 are provided for driving the fluid stored in container 205 out the container's outflow opening 225 and into tube 305. Looking next at FIG. 2, fluid driving means 400 comprises two constant force springs 405A, 405B, each of which is attached to a movable member 410 which engages the floor 215 of container 205. Springs 405A, 405B apply an upward force of a constant magnitude to floor 215 of container 205. This upward force from springs 405A, 405B is sufficient to cause the container's compressible side walls 210 to yield and allow floor 215 to move upward against the container's immovable top 220, which is fixed in place by a support structure 415, thereby driving fluid out of container 205 through outflow opening 225 and, into hollow tube 305. It is to be appreciated that since springs 405A, 405B are constant force springs, the upward force applied to the container's movable floor 215 by springs 405A, 405B will remain constant regardless of the volume of fluid residing inside container 205. Thus it will be seen that fluid driving means 400 are capable of driving fluid out of fluid reservoir 200 and through tubing means 300 at a constant pressure.

Rotating wiper means 500 are provided for generating discrete eyedrops out of the fluid flowing in tube 305 so that discrete eyedrops exit nozzles 335A, 335B and enter the eyes, and for controlling the location of the distal-most portion of the fluid in tubing means 300 between eyedrop ejections, as will hereinafter be discussed in further detail. Looking next at FIG. 3, rotating wiper means 500 comprises a rigid support member 505 having a concave surface 510 formed on one side thereof. In the preferred embodiment of the invention, concave surface 510 is formed with a semi-circular geometry. Hollow tube 305 is positioned against support member 505 so that tube 305 follows the contour of concave surface 510. At least the portion of tube 305 following the contour of concave surface 510, and preferably the entire length of tube 305, is flexible to the point of being easily deformable and compressible, as will hereinafter be described in further detail.

Rotating wiper means 500 also comprises a rotating wiper assembly 515 which is adapted to be mounted on a rotating shaft 520 driven by appropriate motor apparatus (not shown) so that the wiper's one or more arms 525 will rotate about the axis of the shaft and can ride along the contour of concave surface 510. More particularly, each of the arms 525 is provided with an end roller 530 at its periphery, and shaft 520 is positioned and arms 525 sized and shaped so that end rollers 530 will substantially engage and follow the contour of concave surface 510 when the rotating arms pass by rigid support member 505. Preferably this is done by setting the center of rotation of shaft 520 at the center of curvature of concave surface 510, wherein concave surface 510 has a semi-circular geometry. In this way, when the compressible tube 305 is positioned along concave surface 510 and shaft 520 is rotated, arms 525 will periodically engage and compress hollow tube 305 in a travelling engagement along the length of concave surface 510. By properly positioning shaft 520 relative to rigid support member 505 and properly sizing the length of arms 525, arms 525 can totally constrict the flow of fluid through hollow tube 305 at the point of engagement between the arms and the tube. However, by forming hollow tube 305 out of a sufficiently resilient material, tube 305 can quickly return to its unconstricted condition upon the passage of rotating arms 525. End rollers 530 minimize friction between arms 525 and hollow tube 305 during the travelling engagement between arms 525 and tube 305, while still permitting arms 525 to close down tube 305 at the point of engagement.

As a result of the foregoing construction, when fluid is flowing through hollow tube 305 and shaft 520 is rotated, wiper assembly 515 will rotate so as to cause arms 525 to periodically engage and close off, at a travelling point of engagement, the flexible tubing 305 so that fluid flow through tube 305 will be momentarily interrupted at that point of travelling engagement.

It is an essential feature of the present invention that wiper 515 rotate in a direction such that arms 525 travel counter to the flow of fluid leaving container 205 and traveling to nozzles 335A, 335B, in order that rotating wiper means 500 also be able to control the location of the distal-most portion of the fluid in tubing mean 500 between eyedrop ejections, as will hereinafter be discussed in further detail. By way of illustration, in the arrangement shown in FIG. 3 wherein the two nozzles 335A, 335B are represented schematically by a single nozzle 335, shaft 520 would be adapted to rotate in a clockwise direction so that the point of travelling engagement between rollers 530 and tube 305 will also move in a clockwise direction.

Figure 4:
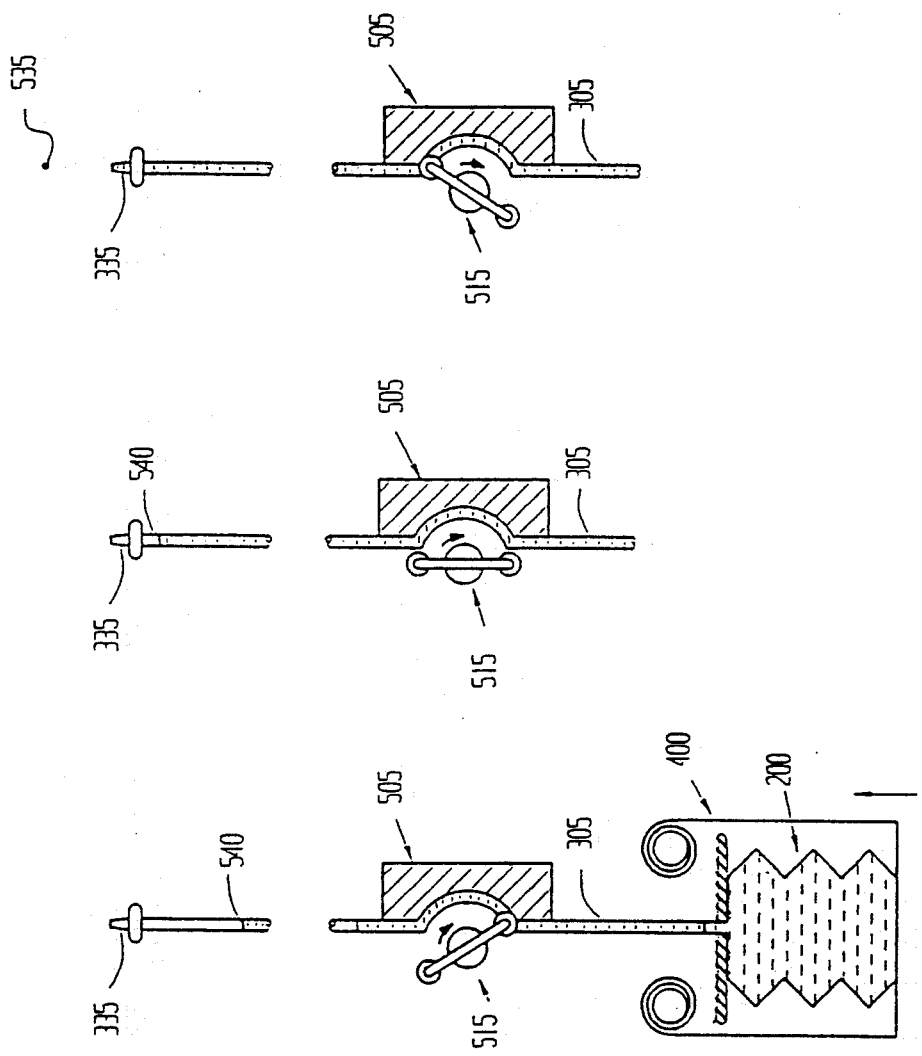
FIGS. 4A-4C are schematic views of selected portions of the system, with the rotating wiper means being shown in a series of different positions.

The operation of rotating wiper means 500 is illustrated in more detail in FIGS. 4A, 4B and 4C.

Looking first at FIG. 4A, rotating wiper means 500 is shown in a first position wherein one of the arms 525 is in engagement with tube 305, such that no fluid is able to pass through the tube to reach the two nozzles 335A, 335B (represented schematically in FIGS. 4A, 4B and 4C by a single nozzle 335). Thus, in the position shown in FIG. 4A, rotating wiper means 500 is effectively acting as a closed gate, preventing fluid from reaching nozzle 335. At the same time, however, eyedrop fluid fills the portion of tube 305 residing between container 205 and the engaging roller 530, and also the portion of the tube residing between the engaging roller 530 and a fluid meniscus 540. It is to be appreciated that the portion of tube 305 extending between fluid meniscus 540 and nozzle 335 is empty of fluid.

When it is time for the system to form and eject an eyedrop (actually two eyedrops, since one eyedrop is ejected from each of the two nozzles 335A, 335B), the rotating wiper means 500 first moves into the position shown in FIG. 4B. More specifically, shaft 520 is rotated in a clockwise direction (as seen from the angle of view of FIGS. 4A, 4B and 4C) so as to move the arm 525 previously engaging tube 305 off the tube, and also so as to keep any of the other arms 525 which may be provided on wiper assembly 515 off the tube. In this way, tube 305 will be free from any constrictions whatsoever, so that it is able to conduct fluid between container 205 and nozzles 335A, 335B. Thus, in the position shown in FIG. 4B, rotating wiper means 500 is effectively acting as an open gate, allowing fluid to move past rotating wiper means 500 to reach nozzles 335A, 335B.

Since fluid driving means 400 are adapted to continuously act on the walls of container 205 to urge the eyedrop fluid in container 205 (and hence the eyedrop fluid in tube 305 as well) to move toward nozzles 335A, 335B, it will be appreciated that when rotating wiper means 500 assume the position shown in FIG. 4B, the fluid in tube 305 will suddenly surge forward toward nozzles 335A, 335B. Thus, in FIG. 4B, it will be seen that the fluid meniscus 540 has moved toward the nozzles. In particular, for the sake of example, the fluid meniscus 540 is shown in FIG. 4B to have almost—but not quite—reached the ends of nozzles 335A, 335B.

Of course, were rotating wiper means 500 to remain permanently in the position shown in FIG. 4B, fluid meniscus 540 would move past the ends of nozzles 335A, 335B and a steady stream of fluid would thereafter be emitted from the nozzles into the eyes of the user. Since the purpose of the present invention is to periodically eject discrete eyedrops of fluid into the eyes of the user, and not a steady stream of fluid, it will be recognized that rotating wiper means 500 are not permitted to remain permanently in the position shown in FIG. 4B.

In fact, at the appropriate moment, after just enough fluid to form one eyedrop 535 (FIG. 4C) has moved past the ends of each of the nozzles 335A, 335B, the rotating wiper means 500 are moved into the position shown in FIG. 4C. More specifically, shaft 520 is rotated once more in a clockwise direction (as seen from the angle of view of FIGS. 4A, 4B and 4C) so as to move an arm 525 back into engagement with tube 305. This will prevent any further fluid from moving past the ends of nozzles 335A, 335B. Thus, in the position shown in FIG. 4C, rotating wiper means 500 are effectively acting once again as a closed gate, preventing any further fluid from passing rotating wiper means 500. At the same time, however, just enough eyedrop fluid will have been allowed to leave nozzles 335A, 335B to form one eyedrop 535 for each nozzle. It is to be appreciated that each of these eyedrops will have sufficient momentum imparted to it by fluid driving means 400 to propel the eyedrops away from the nozzles into the eyes of the user.

Thereafter, rotating wiper means 500 are brought from the position shown in FIG. 4C back to the position shown in FIG. 4A. More particularly, shaft 520 is rotated once more in a clockwise direction (as seen from the angle of view of FIGS. 4A, 4B and 4C) so as to move the engaging arm 525 along the length of concave surface 510. As this occurs, the point of engagement between end roller 530 and flexible tube 305 also moves along the length of concave surface 510, thereby drawing the fluid meniscus 540 inward, away from the ends of nozzles 535A, 535B, to the position shown in FIG. 4A. By drawing the fluid meniscus 540 back into the interior of tubing means 300, so that meniscus 540 is disposed within, and substantially engulfed by, tubing means 300, a super-saturated vapor condition can be created in the interior of tubing means 300, adjacent fluid meniscus 540. The creation of such an environment at the fluid meniscus 540 helps minimize any crystal formation in the distal portion of tubing means 300, e.g. it helps minimize any crystal formation in nozzles 335A, 335B. It is to be appreciated that the precise point within tubing means 300 at which meniscus 540 comes to rest when rotating wiper means 500 are in the position shown in FIG. 4A will depend upon the configuration of various elements of the system, e.g. tubing diameter, travelling engagement stroke, etc. In any case, however, the system is arranged so that meniscus 540 is always disposed within, and substantially engulfed by, tubing means 300 when the rotating wiper means 500 are in the position shown in FIG. 4A, so that the supersaturated vapor condition can be created in the interior of tubing means 300 adjacent fluid meniscus 540.

It is to be appreciated that the frequency, velocity and volume of the eyedrops ejected by the system can be accurately regulated in accordance with the particular needs of the user by adjusting the various system parameters affecting the same, i.e., the fluid pressure produced by the fluid driving means, the configuration and rate of rotation of the rotating wiper assembly 515, the diameter of the tubing and nozzles, the viscosity of the eyedrop fluid, etc.

Figure 5:
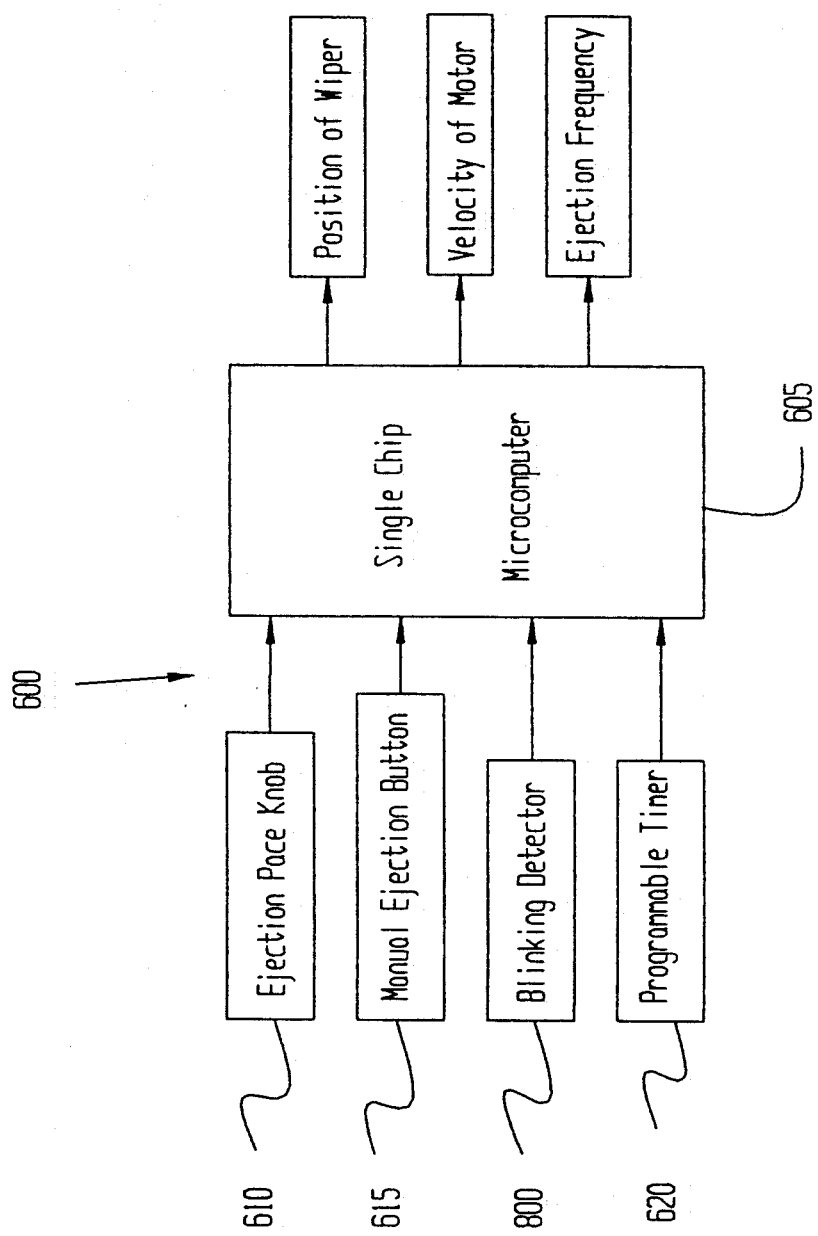
FIG. 5 is a schematic representation of a control system for operating the various components of the eyedrop ejection system.

Control means 600 are also provided for controlling the operation of the various elements of the system. Looking next at FIGS. 1 and 5, control means 600 comprises a programmable microcomputer 605 which interfaces in ways well known in the art between various input controls and various operating elements of the system, whereby the input controls can be used by the user to control the operation of the system. By way of example, the system might comprise an ejection pace knob 610 whereby the frequency of the regular, periodic eyedrop ejection could be set, a manual ejection button 615 whereby the user could override the system to force an immediate eyedrop ejection, and a programmable timer 620 whereby the system could have an eyedrop ejection pattern which changes over time according to a preprogrammed pattern. Microcomputer 605 would be appropriately programmed in ways well known in the art so that depending on the settings of the various input controls, the rotation of wiper assembly 515 would be appropriately controlled so as to properly regulate eyedrop formation.

Looking next at FIGS. 1 and 2, a low reservoir alarm 700 is also provided to indicate when the fluid in container 205 is about to be depleted. Low reservoir alarm 700 comprises a pair of electrical contacts 705 and 710. Contact 705 is mounted to movable member 410 via a bracket 715 so as to move in conjunction with the same, and contact 710 is connected to the support structure 415 via a bracket 720 so as to be fixed in place, whereby contact 705 will approach contact 710 and touch it as the eyedrop fluid in container 205 is depleted. Contacts 705 and 710 are connected into a simple electrical circuit (not shown) such that when they come into contact with one another, they will close the circuit and thereby activate the low reservoir alarm, which can be either an audio or visual signal. By way of example, a low reservoir warning light 725 is shown mounted to housing 15.

Preferably the system also comprises eye and eyelid detecting means 800 for detecting the positions of the eyes and eyelids prior to eyedrop ejection and preventing eyedrop ejection when the eyes are in a disadvantageous position or the eyelids are closed. Looking next at FIGS. 1, 5 and 6A, 6B and 6C, eye and eyelid detecting means 800 generally comprise a pair of photodiodes 805A, 805B, and a pair of phototransistors 810A, 810B. Each of the photodiodes 805A, 805B emits a tiny beam of light 815 which strikes the eye at precisely the spot where the eyedrop ejected by nozzles 335A, 335B will contact the eye. As seen in FIG. 6A, when incident light beams 815 strike the large white sclera of the eye, strong reflective light beams 820 will return, with the reflective beams 820 striking phototransistors 810A, 810B. When phototransistors 810A, 810B receive the reflective beams 820, they signal the microcomputer 605 that the eyes and eyelids are properly positioned to receive the eyedrops, and microcomputer 605 then allows the eyedrop ejection to proceed as planned.

However, if, as seen in FIG. 6B, the eyes should be positioned so that the pupils are directed straight towards the nozzles 335A, 335B, or if, as seen in FIG. 6C, the eyelids should be closed (or insufficiently open), little or no reflective light beams 820 will be received by phototransistors 810A, 810B. As a result, phototransistors will report the same to microcomputer 605. In this case, microcomputer 605 would then intercede to prevent eyedrop ejection from proceeding until phototransistors once again reported the proper receipt of reflective beams 820. In this way, eye and eyelid detecting means 800 will ensure that the system will only eject eyedrops towards the eyes when the eyes are open and not looking directly at the nozzles 335A, 335B.

The various electrical components of the present invention are intended to be driven by a battery, and in the preferred embodiment of the present invention a visual low battery indicator 899 (FIG. 1) of the sort well known in the art is provided.

Figure 7:
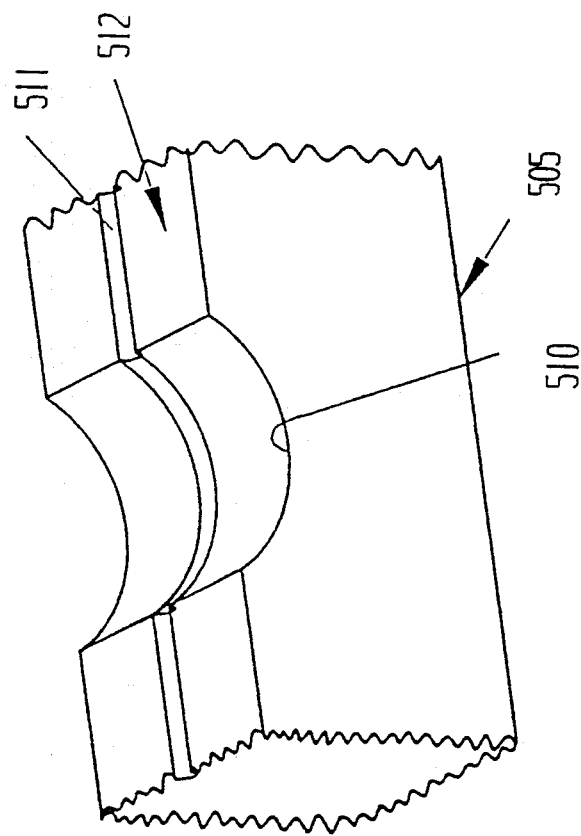
FIG. 7 is a partial perspective view showing a modified form of part of the fluid control means.

Looking next at FIG. 7, it has also been found helpful in some circumstances to form a shallow groove 511 on rigid support block 505 to act as a seat for hollow tube 305. To this end, it will be appreciated that groove 511 will follow the geometry of the support block's surface 512 and extend along the concave surface 510. By seating tube 305 in groove 511, the tube will be better retained in place during engagement of wiper assembly 515 with the tube, and lateral movement of tube 305 will be inhibited. Of course, it will also be appreciated that groove 511 must be formed very shallow in depth relative to the dimensions of tube 305 in order that the wiper assembly 515 not be inhibited from completely closing off the tube during engagement of the wiper assembly with the tube.

It is also to be appreciated that hollow tube 305 is held in position against block 505, ready for engagement by wiper assembly 515, by means of the sort well known in the art, e.g. tube 305 could be cemented to block 505 using a resilient cement, or tube 305 could be clamped to block 505 using ordinary mechanical clamping means of the sort well known in the art. Of course, in the event mechanical clamping means are used, care must be taken to make a secure engagement between the mechanical clamping means and the hollow tube 305 without constraining the flow of fluid through the tube.

It will also be appreciated that certain changes may be made to the preferred embodiment just described without departing from the scope of the present invention.

Thus, for example, in the preferred embodiment of the invention just described, rotating wiper means 500 comprises a wiper assembly 515 rotatably mounted on a shaft 520, wherein the shaft is driven by an appropriate motor (not shown). Alternatively, it is also anticipated that the rotation of shaft 520 might be controlled by some means other than a motor, e.g. it might be controlled by an element formed out of a shape memory alloy such as Nitinol. In such a situation, the temperature-sensitive shape memory alloy would be configured in ways well known in the art and its temperature manipulated as needed so that the resulting changes in the element's shape would move rotating wiper means 500 through its various positions as shown in FIGS. 4A, 4B and 4C. Alternatively, other shaft-driving mechanisms of the sort well known in the art could be employed.

It is also anticipate that driving means 400 and rotating wiper assembly 500 might be replaced with alternative structure.

More particularly, in its broadest form, the present invention requires a fluid reservoir for holding a supply of the eyedrop fluid, tubing means for conducting the fluid from the fluid reservoir to the eyes, and fluid control means for selectively (1) driving the fluid from the fluid reservoir through the tubing means so that discrete eyedrops exit the distal end of the tubing means and are administered to the eyes, and (2) withdrawing the fluid remaining in the tubing means away from the distal end of the tubing means so that the distal-most portion of the fluid is disposed within, and is substantially engulfed by, the tubing means, whereby the distal-most portion of the fluid may create a super-saturated vapor condition at that point in the tubing means. In this respect, in the preferred embodiment of the invention, the tubing means comprises a resilient hollow tube 305, and the fluid control means comprises driving means 400 for continuously driving fluid from the fluid reservoir towards the eyes, and rotating wiper means 500 for selectively engaging the tube so as to press against it and close it off at the point of engagement. By arranging rotating wiper means 500 so that it engages the tube along a travelling point of engagement, wherein the point of engagement travels in a direction opposite to the flow of fluid through the tube, rotating wiper means 500 can act as both a gate for releasing fluid driven by driving means 400, and as a reverse drive mechanism for withdrawing the fluid remaining in the tubing means away from the distal end of the tubing means between eyedrop ejections.

Figure 8:
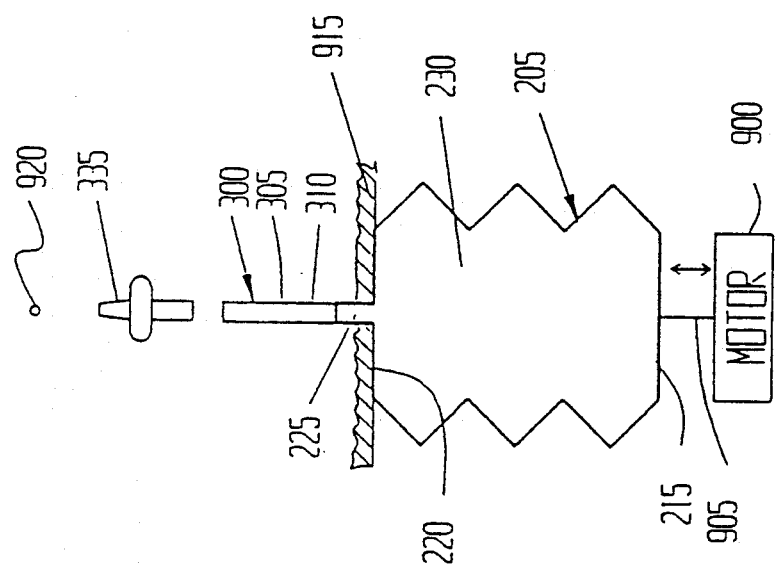
FIG. 8 is a schematic view showing an alternative form of the fluid control means.

FIG. 8 shows an alternative structure, wherein no driving means 400 are provided about fluid reservoir 200, and no rotating wiper means 500 are provided intermediate tubing means 300. Instead, a motor 900 engages the movable floor 215 of the bellows-type container 205 via a linkage 905 of the sort well known in the art so as to alternatively move the container's floor 215 towards and away from the immovable top 220 of the container on command. (Immovable top 220 is fixed in place by a support structure 915 which is substantially the same as the support structure 415 previously disclosed.) By moving the floor 215 of the container towards the top 220, motor 900 will cause the volume of the container to contract, thereby sending a surge of fluid out of the container and down tubing means 300 toward the eyes. As soon as this surge has caused a single eyedrop 920 of proper size to fly off the ends of nozzles 335A, 335B (represented schematically by a single nozzle 335 in FIG. 8), motor 900 will move the floor 215 of the container away from its top 220 so as to cause the volume of the container too increase, thereby sucking the fluid remaining in tubing means 300 away from the ends of nozzles 335A, 335B and back toward container 205. Motor 900 is adapted to cause the volume of the container to increase sufficiently much so that the fluid meniscus residing at the distal-most portion of the fluid remaining in tubing means 300 will be withdrawn sufficiently far into tubing means 300 that the meniscus is disposed within, and is substantially engulfed by, the tubing means, whereby the distal-most portion of the fluid may create a super-saturated vapor condition at that point in the tubing means.

Of course, it will be appreciated that with the embodiment disclosed in FIG. 8, motor 900 and/or its associated linkage 905 could be replaced with alternative structure of the sort well known in the art, e.g. motor 900 could be replaced by a different sort of actuator, such as a piezoelectric crystal arrangement, or a shape memory alloy actuator, or an electric or pneumatic linear actuator, or some other equivalent means for creating reciprocating linear motion to be transferred to the container 205.

It will also be appreciated that with the embodiment shown in FIG. 8, tubing means 300 need not have any of its length formed out of flexible tubing, since with this embodiment there is no need to compress the tube to regulate eyedrop formation or meniscus positioning within the tubing means 300.

Still other changes may be made to the disclosed embodiments without departing from the scope of the present invention.

ADVANTAGES OF THE INVENTION

Numerous advantages are achieved by using the present invention.

The present invention provides a new and improved eyedrop delivery system which is portable.

In addition the present invention provides a new and improved eyedrop delivery system which is simple to use and maintain.

Also, the present invention provides a new and improved eyedrop delivery system which is comfortable to wear and use.

Additionally, the present invention provides a new and improved eyedrop delivery system which will automatically administer eyedrops to the eyes at a programmable rate.

Furthermore, the present invention provides a new and improved eyedrop delivery system which will administer eyedrops to the eyes on demand.

In addition, the present invention provides a new and improved eyedrop delivery system which controls the velocity, volume and frequency of the eyedrop ejection.

The present invention also provides a new and improved eyedrop delivery system which can detect eye and eyelid position and condition.

Also, the present invention provides a new and improved eyedrop delivery system which is clog free.

A further advantage of the present invention is that it provides a new and improved eyedrop delivery system which is inexpensive.

In addition, the present invention provides a new and improved eyedrop delivery system which is able to deliver eyedrops to both eyes simultaneously.

What is claimed is:

1. An eyedrop delivery system for administering eyedrops to at least one eye of a user, said system comprising:
    a fluid reservoir for holding a supply of eyedrop fluid;
    tubing means for conducting eyedrop fluid from said fluid reservoir to at least one eye of the user, said tubing means comprising at least one distal end portion adapted to terminate adjacent the at least one eye of the user;
    fluid driving means for continuously urging eyedrop fluid from said fluid reservoir through said tubing means toward said at least one distal end portion of said tubing means; and
    fluid control means for successively:
        (1) permitting eyedrop fluid to flow freely through said tubing means so that eyedrop fluid can begin to exit said at least one distal end portion of said tubing means,
        (2) interfering with the flow of eyedrop fluid through said tubing means so as to prohibit any further eyedrop fluid from exiting said at least one distal end portion of said tubing means, and so as to cause the eyedrop fluid beginning to exit said at least one distal end portion of said tubing means to exit said at least one distal end portion of said tubing means as a discrete eyedrop, and
        (3) withdrawing the eyedrop fluid remaining in said tubing means away from said at least one distal end portion of said tubing means so that the distal-most portion of the eyedrop fluid is disposed within, and is substantially engulfed by, said tubing means so the distal-most portion of the eyedrop fluid may create a super-saturated vapor condition at that point in said tubing means.

2. An eyedrop delivery system according to claim 1 wherein said fluid reservoir comprises a bellows-type container.

3. An eyedrop delivery system according to claim 1 wherein said fluid reservoir comprises a bellows-type container having compressible side walls, a movable floor, and an immovable lid having an outflow opening, and further wherein said fluid driving means comprises means for moving said floor toward said lid.

4. An eyedrop delivery system according to claim 3 wherein said means for moving said floor toward said lid comprises a constant force spring.

5. An eyedrop delivery system according to claim 1 wherein said tubing means comprises a resilient hollow tube portion,
    and further wherein said fluid control means comprises movable wiper means for successively:
        1) not engaging said resilient hollow tube portion;
        2) engaging said resilient hollow tube portion so as to press against it and close it off at the point of engagement, and
        3) engaging said resilient hollow tube portion along a travelling point of engagement which moves in a direction opposite to the flow of fluid through said resilient hollow tube portion away from said point of engagement.

6. An eyedrop delivery system according to claim 5 wherein said movable wiper means moves in a rotating arc, and further wherein said resilient hollow tube portion is positioned substantially tangentially to said rotating arc.

7. An eyedrop delivery system according to claim 6, wherein said movable wiper means comprises a rotating shaft, at least one arm attached to said rotating shaft so as to rotate therewith, and a support block having a concave surface thereof, said resilient hollow tube portion residing against said concave surface, and said shaft, said at least one arm, said resilient hollow tube and said support block being sized and positioned so that said at least one arm will engage and close off said resilient hollow tube portion along the travelling point of engagement when said shaft is rotated.

8. An eyedrop delivery system according to claim 7 wherein said support block has a shallow groove formed in said concave surface, said shallow groove being sized to provide a seat for said resilient hollow tube portion such that said resilient hollow tube portion extends out of said shallow groove when said resilient hollow tube portion resides in said shallow groove.

9. An eyedrop delivery system according to claim 1 wherein said fluid reservoir comprises a bellows-type container, and said fluid driving means comprises means for contracting the volume of said bellows-type container.

10. An eyedrop delivery system according to claim 1 wherein said system further comprises a microcomputer means for operating said fluid control means.

11. An eyedrop delivery system according to claim 1 wherein said system further comprises eye and eyelid detecting means for detecting the position of the at least one eye of the user and the position of its associated eyelid prior to eyedrop ejection and preventing eyedrop ejection when the at least one eye of the user is in a disadvantageous position or when its associated eyelid is closed.

12. An eyedrop delivery system according to claim 11 wherein said eye and eyelid detecting means comprises at least one light beam source and at least one light beam detector.

13. An eyedrop delivery system according to claim 1 wherein said system further comprises support means for supporting said at least one distal end portion of said tubing means adjacent the at least one eye of the user, said support means being adapted to be worn about the head of the user and comprising adjustable means for adjusting the position of said at least one distal end portion of said tubing means relative to the at least one eye of the user.

14. An eyedrop delivery system according to claim 1 wherein said system further comprises operating means for operating said fluid control means so as to cause said eyedrop delivery system to automatically administer an eyedrop to the at least one eye of the user according to a predetermined pattern.

15. An eyedrop delivery system according to claim 1 wherein said system further comprises operating means for operating said fluid control means so as to cause said eyedrop delivery system to administer an eyedrop to the at least one eye of the user.

16. A method for delivering eyedrops to at least one eye of a user, said method comprising the steps of:

(1) providing an eyedrop delivery system comprising:
a fluid reservoir for holding a supply of eyedrop fluid;
tubing means for conducting eyedrop fluid from said fluid reservoir to at least one eye of the user, said tubing means comprising at least one distal end portion adapted to terminate adjacent the at least one eye of the user;
fluid driving means for continuously urging eyedrop fluid from said fluid reservoir through said tubing means toward said at least one distal end portion of said tubing means; and
fluid control means for successively:
(i) permitting eyedrop fluid to flow freely through said tubing means so that eyedrop fluid can begin to exit said at least one distal end portion of said tubing means,
(ii) interfering with the flow of said eyedrop fluid through said tubing means so as to prohibit any further eyedrop fluid from exiting said at least one distal end portion of said tubing means, and so as to cause the eyedrop fluid beginning to exit said at least one distal end portion of said tubing means to exit said at least one distal end portion of said tubing means as a discrete eyedrop, and
(iii) withdrawing the eyedrop fluid remaining in said tubing means away from said at least one distal end portion of said tubing means so that the distal-most portion of the eyedrop fluid is disposed within, and is substantially engulfed by, said tubing means so that distal-most portion of the eyedrop fluid may create a super-saturated vapor condition at that point in said tubing means;

(2) continuously urging eyedrop fluid from said fluid reservoir through said tubing means toward said at least one distal end portion of said tubing means with said fluid driving means;

(3) causing said fluid control means to permit eyedrop fluid to flow freely through said tubing means so that eyedrop fluid can begin to exit said at least one distal end portion of said tubing means;

(4) causing said fluid control means to interfere with the flow of said eyedrop fluid through said tubing means so as to prohibit any further eyedrop fluid from exiting said at least one distal end portion of said tubing means, and so as to cause the eyedrop fluid beginning to exit said at least one distal end portion of said tubing means to exit said at least one distal end portion of said tubing means as a discrete eyedrop;

(5) causing said fluid control means to withdraw the eyedrop fluid remaining in said tubing means away from said at least one distal end portion of said tubing means so that the distal-most portion of the eyedrop fluid is disposed within, and is substantially engulfed by, said tubing means so the distal-most portion of the eyedrop fluid may create a super-saturated vapor condition at that point in said tubing means; and (6) thereafter repeating Steps (3), (4) and (5) in sequence whenever it is desired to administer another eyedrop to the at least one eye of the user.

17. An eyedrop delivery system for administering eyedrops to at least one eye of a user, said system comprising:
a fluid reservoir for holding a supply of eyedrop fluid;
tubing means for conducting eyedrop fluid from said fluid reservoir to at least one eye of the user, said tubing means comprising at least one distal end portion adapted to terminate adjacent the at least one eye of the user; and
fluid control means for selectively (1) driving eyedrop fluid from said fluid reservoir through said tubing means so that discrete eyedrops exit said at least one distal end portion of said tubing means and are administered to the at least one eye of the user, and (2) withdrawing the fluid remaining in said tubing means away from said at least one distal end portion of said tubing means so that the distal-most portion of the fluid is disposed within, and is substantially engulfed by, said tubing means so the distal-most portion of the fluid may create a supersaturated vapor condition at that point in said tubing means;

wherein said tubing means comprises a resilient hollow tube portion, and further wherein said fluid control means comprises driving means for continuously driving eyedrop fluid from said fluid reservoir toward said at least one distal end portion of said tubing means, and rotating wiper means for selectively engaging said resilient hollow tube portion so as to press against it and close it off at the point of engagement.

18. An eyedrop delivery system according to claim 17 wherein said rotating wiper means further engages said resilient hollow tube portion along a travelling point of engagement, which travels in a direction opposite to the flow of eyedrop fluid through said resilient hollow tube portion away from the point of engagement.

19. An eyedrop delivery system according to claim 18 wherein said rotating wiper means comprises a rotating shaft and at least one arm attached to said rotating shaft so as to rotate therewith, and a support block having a concave surface thereon, said resilient hollow tube portion residing against said concave surface; and said shaft, said at least one arm, said resilient hollow tube portion and said support block being sized and positioned so that said at least one arm will engage and close off said resilient hollow tube portion along the travelling point of engagement when said shaft is rotated.

20. An eyedrop delivery system according to claim 19 wherein said support block has a shallow groove formed in the concave surface, said groove being sized to provide a seat for said resilient hollow tube portion.

* * * * *

UNITED STATES PATENT AND TRADEMARK OFFICE
CERTIFICATE OF CORRECTION

PATENT NO. : 5,171,306

DATED : 12/15/92

INVENTOR(S) : Vo, Van Toi

It is certified that error appears in the above-identified patent and that said Letters Patent is hereby corrected as shown below:

Claim 16, column 14, line 22, the word "that" should be -- the --.

Signed and Sealed this

Second Day of November, 1993

Attest:

BRUCE LEHMAN

Attesting Officer

Commissioner of Patents and Trademarks